United States Patent [19]

Wegman et al.

[11] Patent Number: 4,727,200

[45] Date of Patent: Feb. 23, 1988

[54] ALCOHOL HOMOLOGATION

[75] Inventors: Richard W. Wegman, South Charleston; Kenneth G. Moloy, Charleston, both of W. Va.

[73] Assignee: Union Carbide Corporation, Danbury, Conn.

[21] Appl. No.: 30,741

[22] Filed: Mar. 27, 1987

[51] Int. Cl.$^4$ .................... C07C 29/00; C07C 29/14; C07C 31/08; C07C 33/22

[52] U.S. Cl. .................... 568/902; 568/715; 568/808

[58] Field of Search .................... 568/902 H, 808, 715

[56] References Cited

U.S. PATENT DOCUMENTS

| | | | |
|---|---|---|---|
| 3,248,432 | 4/1966 | Riley et al. | 568/902 H |
| 3,285,948 | 11/1966 | Butter et al. | 568/902 H |
| 3,387,043 | 6/1968 | Kuraishi et al. | 568/902 H |
| 3,769,329 | 10/1973 | Paulik et al. | 260/488 K |
| 3,972,952 | 8/1976 | Clark | 568/902 H |
| 4,111,837 | 9/1978 | Taylor | 568/902 H |
| 4,133,966 | 1/1979 | Pretzer et al. | 568/902 H |
| 4,168,391 | 9/1979 | Slinkard et al. | 568/902 H |
| 4,170,605 | 10/1979 | Williamson et al. | 260/449 L |
| 4,190,729 | 2/1980 | Foster | 568/902 H |
| 4,233,466 | 11/1980 | Fiato | 568/902 H |
| 4,277,634 | 7/1981 | Walker | 568/902 H |
| 4,328,375 | 5/1982 | Barlow | 568/902 H |
| 4,352,947 | 10/1982 | Habib et al. | 568/902 H |
| 4,355,192 | 10/1982 | Cornils et al. | 568/902 H |
| 4,386,009 | 5/1983 | Feder et al. | 568/902 H |
| 4,389,532 | 6/1983 | Larkins et al. | 568/902 H |
| 4,393,255 | 7/1983 | Mitchell et al. | 568/902 H |
| 4,405,815 | 9/1983 | Keim et al. | 568/902 H |
| 4,424,383 | 1/1984 | Cornils et al. | 568/902 H |
| 4,472,526 | 9/1984 | Cornils et al. | 568/902 H |
| 4,514,336 | 4/1985 | Ryan et al. | 568/902 H |
| 4,540,836 | 9/1985 | Fenton | 568/902 H |
| 4,552,986 | 11/1985 | Isogai et al. | 568/902 H |

FOREIGN PATENT DOCUMENTS 2036739  7/1980  United Kingdom ............ 568/902 H

OTHER PUBLICATIONS

I. Wender et al., Science, 206-207, (Feb. 23, 1951), Ethanol from Methanol.

J. Berty et al., Chem. Tech., 9, 283-286, (May, 1957), Synthese von Octylalkohol aus Crackbenzin mit Kohlenoxyd und Wasserstoff.

M. Fakley et al., Applied Catalysis, 5, 3-18, (1983), The Catalytic Hydrocarbonylation of Alcohols—A Review.

W. Pretzer et al., Ann. N.Y. Acad. Sci. A, 333, 58-66, (1980), Methanol Carbonylation as an Alternate Route to Chemicals.

A. Deluzarche et al., Kohle Erdgas Petrochem., 32, 436-438, (1979), Reaction Between CO, $H_2$, $CH_3OH$.

H. Dumas et al., J. Organomet. Chem., 177, 239, (1979), XII. Homologization of Methanol by Homogeneous Rhodium Derivative Catalysts.

M. J. Chem et al., Catalysis of Organic Reactions, W. R. Asser, Ed. Marcel Dekker, Inc. 273-288, (1981), Mechanism of a New Process for Methanol Homologation.

T. Mizorogi, Shokubai (Catalysts), 19, 90-95, (1977), Synthesis of $C_2$-Containing Oxygeneous Compounds by Utilizing Carbon Monoxide.

M. Roper et al., Catalysis in $C_2$ Chemistry, W. Kevin, Ed., D. Reidel Pub. Co., 105-134, (1983), The Homologation of Methanol.

*Primary Examiner*—J. E. Evans
*Attorney, Agent, or Firm*—R. J. Finnegan

[57] ABSTRACT

A process for the homologation of an alkanol by reaction with synthesis gas in contact with a system containing rhodium atom, ruthenium atom, iodine atom and a bis(diorganophosphino) alkane to selectivity produce the next higher homologue.

28 Claims, No Drawings

ALCOHOL HOMOLOGATION

The Government of the United States of America has rights in this invention pursuant to Contract No. DE-AC22-84PC70022 awarded by the U.S. Department of Energy.

FIELD OF INVENTION

This invention relates to the homologation of an alkanol, e.g., methanol, by reaction with synthesis gas in contact with a catalyst system comprising rhodium atom, ruthenium atom, halogen atom and certain defined bis(diorganophosphino) alkane ligands.

DESCRIPTION OF THE PRIOR ART

The manufacture of organic compounds from synthesis gas, a mixture of hydrogen and carbon monoxide, is well known. For example, methanol has been made from synthesis gas and then further reacted with synthesis gas in homologation, hydroformylation or carbonylation reactions to produce oxygenated compounds. These reactions are well known and many catalyst systems have been disclosed based on the Group VIII transition metal compounds. Thus it has been shown that rhodium-based catalyst systems can be used to carbonylate methanol to acetic acid: cobalt-based catalyst systems will cause a reductive carbonylation of methanol to acetaldehyde: ruthenium-cobalt-based catalyst systems will homologate methanol to ethanol; and cobalt-based catalyst systems will homologate methanol to ethanol. Generally, the processes employ an iodine promoter and a phosphorus-containing ligand.

The carbonylation reaction is illustrated by the reaction of methanol with CO to form acetic acid using either a Rh-I or a Co-I catalyst:

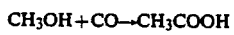

CH₃OH+CO→CH₃COOH

Hydroformylation or reductive carbonylation is illustrated by reaction of methanol with synthesis gas to form acetaldehyde; this reaction can be conducted using a Co-I catalyst or a Rh-I-PR₃ (bidentate phosphorus compound) as the catalyst:

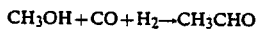

CH₃OH+CO+H₂→CH₃CHO

The homologation reaction is illustrated by the reaction of methanol with synthesis gas to form ethanol; this reaction is traditionally carried out using a Co-Ru-I catalyst:

CH₃OH+CO+H₂→C₂H₅OH

The three reactions are carried out at elevated temperatures and pressures as high as 10,000 psig have been reported. Many variations have been reported, not only in the temperatures and pressures used, but in modifications made to the catalyst systems and additives introduced into the reactor.

To the best of our knowledge, however, there has not heretofore been suggested or disclosed a rhodium-based homologation catalyst system that generates ethanol selectively and at high rates from methanol and synthesis gas at mild pressure and temperature conditions. Several of the pertinent publications and patents in the area are discussed below.

A cobalt-based catalyst is used in U.S. Pat. No. 3,248,432 issued to A. D. Riley et al. on Apr. 26, 1966, to produce ethanol. In this reference methanol is reacted with carbon monoxide and hydrogen at a pressure in excess of 3,000 to 4,000 psi and a temperature of from about 150° C. to 250° C. in the presence of a modified catalyst complex containing cobalt, an iodine promoter and a phosphorus compound as defined. In essence this is a homologation process using a cobalt-based catalyst.

Another homologation process is disclosed in U.S. Pat. No. 3,285,948 issued to C. N. Butter et al. on Nov. 15, 1966. This patent discloses the use of halides of ruthenium and osmium as second promoters in conjunction with cobalt and iodine for the production of ethanol by the homologation reaction of methanol with carbon monoxide and hydrogen.

The invention claimed in U.S. Pat. No. 3,387,043 issued to M. Kuraishi et al. on June 4, 1968 is the improvement of adding water to the homologation reaction of ethanol, n-propanol or n-butanol with carbon monoxide and hydrogen using a catalyst containing cobalt and iodine.

A solid, heterogeneous catalyst is used in the homologation reaction disclosed in U.S. Pat. No. 3,972,952 issued to R. T. Clark on Aug. 3, 1976. The catalytic agent is a base promoter such as an oxide, hydroxide or salt of the alkali and alkaline earth metals and a metal of the group ruthenium, rhodium, palladium, osmium, iridium and platinum on an inert solid support material comprising alumina. In this process an alkanol is converted to a higher alkanol.

In U.S. Pat. No. 4,111,837 issued to P. D. Taylor on Sept. 5, 1978, methanol is reacted in liquid phase with carbon monoxide and hydrogen at a temperature of from 100° C. to 350° C. and a pressure of from 1,000 to 15,000 psi in the presence of a heterogeneous catalyst containing a cobalt derivative and a methanol-insoluble rhenium derivative.

The homologation of methanol with carbon monoxide and hydrogen to produce ethanol is described in U.S. Pat. No. 4,133,966 issued to W. R. Pretzer et al. on Jan. 9, 1979. In the process disclosed the catalyst system is cobalt acetylacetonate a tertiary organo Group VA compound, an iodine compound as a first promoter and ruthenium compound as a second promoter.

The homologation of methanol with synthesis gas in the liquid phase using a cobalt carbonyl catalyst is disclosed in U.S. Pat. No. 4,168,391 issued to W. E. Slinkard et al. on Sept. 18, 1979. The improvement claimed in this patent is the use of a non-polar, substantially inert, oxygenated hydrocarbon solvent that does not coordinate strongly with cobalt carbonyl as the solvent during the reaction.

A ruthenium based catalyst is disclosed in U.S. Pat. No. 4,170,605 issued to R. C. Williamson et al. on Oct. 9, 1979; however, the process is one which selectively produces ethylene glycol, not alkanols.

Homologation is also disclosed in U.S. Pat. No. 4,190,729 issued to D. Foster on Feb. 26, 1980, in which a tertiary phosphine oxide is used as a stabilizer during the homologation reaction of methanol to ethanol, acetaldehyde and methyl acetate employing a cobalt-based catalyst.

The selective production of ethanol by the homologation of methanol with carbon monoxide and hydrogen under selected ratios and reaction conditions catalyzed by cobalt, ruthenium, an iodine promoter, and a phosphine ligand as shown in U.S. Pat. No. 4,233,466 issued to R. A. Fiato on Nov. 11, 1980.

In U.S. Pat. No. 3,769,329, issued to Paulik et al. on Oct. 30, 1973, there is reported a process for the carbonylation of compounds, including alcohols, by reaction with carbon monoxide in contact with a catalyst system containing a rhodium component and a halogen component. The reaction produces acids and esters. Though a rhodium-based catalyst system is used in the ethanol-carbon monoxide reaction the examples show no indication of homologation. In Example 5 it is specifically stated "This example demonstrates the reaction may be carried out in the presence of a carbon monoxide stream containing significant quantities of hydrogen without the formation of undesirable products such as acetaldehyde, ethanol, or catalyst decomposition". Had homologation occurred, ethanol would have been formed in this example in which methanol feedstock was reacted with synthesis gas in contact with a rhodium catalyst; essentially the only product produced was acetic acid via a carbonylation reaction.

U.S. Pat. No. 4,277,634, issued to Walker on July 7, 1981, discloses the homologation of methanol to ethanol using a cobalt-containing catalyst system in the presence of specific inert solvents to improve selectivity.

U.S. Pat. No. 4,389,532, issued to Larkins et al. on June 21, 1983, discuss a Co-Pt-I catalyst system in which the Pt is alleged to have a stabilizing effect on the cobalt-iodide system. At column 3, lines 55 et seq., they state that other metals, e.g., rhodium and ruthenium, do not demonstrate this stabilizing quality. The process described is basically one for the preparation of acetaldehyde.

U.S. Pat. No. 4,424,383 and U.S. Pat. No. 4,472,526, both issued to Cornils et al. on Jan. 3, 1984 and Sept. 18, 1984, respectively, deal with the production of ethanol and propanol from methanol. Both employ a cobalt compound, a ruthenium compound, iodine or an iodide and a phosphorus compound, the latter differing in the two patents. The phosphorus compounds include the bis(diorganophosphino) alkane ligands employed by applicant. However, the references do not use a rhodium based catalyst as is required by applicant.

U.S. Pat. No. 4,514,336, issued to Ryan et al. on Apr. 30, 1985, discuss a process for producing acids by reacting an alcohol with synthesis gas using a catalyst containing ruthenium-rhodium-iodide-titanium (IV). The patent contains no mention of the bis(diorganophosphino) alkane compounds or ligands and does not suggest or disclose the possibility of selective formation of ethanol and its equivalents. Nor would the combination of the teachings of this reference with the teachings of the Cornils et al. references suggest it. The references teach that a ruthenium-rhodium-containing system produces acids and that the phosphorus ligands can be used to improve synthesis gas reactions. One skilled in the art might consider the use of the ligands disclosed by the Cornils et al. references in the acid-forming catalytic reaction of the Ryan et al. reference but this would not suggest the ethanol-formation process of this application. There is nothing to suggest, nor is there any disclosure, in these references to the new, unexpected and unpredicted discovery for the production of alkanols described in this instant application.

I. Wender et al, Science, 206 (Feb. 23, 1951) reported the homologation of methanol to ethanol using a cobalt carbonyl catalyst. Their work was the initial breakthrough in this area. Similar work was subsequently performed and reported by J. Berty et al., Chem. Tech., 9, 283 (1957).

M. Fakley et al., Applied Catalysis, 5, 3 (1983) discuss the reaction of methanol with synthesis gas using metal compound catalysts. On page 4 they indicate their preference of the use of the term "hydrocarbonylation" rather than "homologation". On page 5, they state: "Rhodium, often appreciably more active than cobalt in other reactions involving $CO/H_2$, produces acids and esters with ethanol becoming a significant product of rather high $H_2$ partial pressures ($H_2/CO=40:1$)". In essence the authors indicate that rhodium catalysts favor production of acids and esters and extreme $H_2/CO$ ratios are necessary to obtain any meaningful quantity of ethanol. Further, nowhere do they suggest a mixture of rhodium and ruthenium in combination with the critical bis(diorganophosphino) alkanes defined in this instant specification.

W. Pretzer et al., Ann. N.Y. Acad. Sci. A, 333, 58 (1980), discuss the homologation of methanol with synthesis gas using a $Co-I-PR_3$ system in which the major product is generally ethanol. The authors do refer to the use of rhodium as a known carbonylation catalyst.

A. Deluzarche et al., Kohle Erdgas Petrochem., 32, 436 (1979), examined other catalysts based on iron, rhodium, ruthenium and nickel in the homologation reaction of methanol with synthesis gas. They reported that cobalt was the best homologation catalyst and the four other metals produced essentially no ethanol, an indication that they did not promote the homologation reaction. This is seen from the data presented in Table I on page 437. The yield of ethanol using cobalt catalyst was as high as 25.8 percent, whereas the yields from the other metals ranged from 0.1 to 2.

H. Dumas et al., J. Organomet. Chem., 177, 239 (1979), show the use of a rhodium catalyst. Ethanol was produced in small amounts at low rate and high, 40:1, $H_2:CO$ mole ratio. In practice, such high ratio would be commercially impractical.

M. J. Chen et al., J. Am. Chem. Soc., 104, 7346 (1982), reported on the use of iron-amine based catalyst systems for the homologation reaction. On page 274 they state "the economic viability of the cobalt-based processes is still in some doubt ---", an indication that even in 1982 there was a need to replace the cobalt-based systems with improved systems.

T. Mizoragi et al., Shokubai (Catalysts), 19, 90 (1977), report their study of the reaction of methanol with synthesis gas using catalysts based on cobalt, rhodium and iridium. They report if rhodium is used instead of cobalt catalyst, with methyl iodide promoter, acetic acid is obtained in high yield under relatively mild conditions. They state "The significant differences of Rh catalysts from the Co catalysts is the fact that the hydrogen in the CO gas does not affect the rate of the acetic acid formation nor the selectivity as long as the CO pressure is high. Thus, in the case of the Co-iodine catalyst, the hydrogen molecule is easily activated to form acetaldehyde, whereas in the case of the Rh-methyl iodide catalyst, the hydrogen molecule is not activated." The authors also discussed a Rh-metal solid catalyst supported on $SiO_2$ (Table 2) previously reported and their experiments with this catalyst.

In "Catalysis in $C_1$ Chemistry" edited by Wilhelm Keim and published by D. Reidel Publishing Company (1983), M. Roper et al. discuss "The Homologation of Methanol" pages 105–134. Essentially the entire treatise is devoted to cobalt catalysts; ruthenium catalysts are separately discussed on pages 129 to 130 and rhodium catalysts are separately discussed on pages 130 to 131.

In the section on rhodium catalysts the authors report even when a 1:1 mixture of $H_2:CO$ is used, "selective formation of acetic acid occurs and virtually no hydrogenated by products, such as ethanol or acetaldehyde, are detected". The authors also refer to the Deluzarche et al. and Dumas et al. articles referred to previously and the difficulties these researchers experienced in their efforts to obtain ethanol.

Though the use of cobalt catalysts, ruthenium catalysts, rhodium catalysts and various combinations of these catalysts in processes for the reaction of synthesis gas with other compounds has been extensively documented there is no record of the use of a catalyst system employing both rhodium atom and ruthenium atom in conjunction with the ligand $R_2PXPR_2$, as hereinafter defined, in a homologation process. None of the references discussed above show the use of this ligand in such process, nor does any reference suggest its use in such process.

SUMMARY OF THE INVENTION

The process of this invention is based on the discovery that certain rhodium-based homologation catalyst systems selectively generate the next higher alkanol homologue by the reaction of an alkanol with synthesis gas, e.g., ethanol from the reaction of methanol with synthesis gas. This process was completely unexpected since rhodium-based catalyst systems are not considered homologation catalysts but carbonylation catalysts used in reactions for the production of aldehydes and acids. In the process of the present invention the catalyst system contains rhodium atom, ruthenium atom, halogen atom (preferably iodine) and a bis(diorganophosphino) alkane ligand. The ligand, hereinafter defined, is a critical component of the catalyst system. For simplicity the present process will be described by the homologation of methanol to ethanol, it being understood it applies to all R'OH compounds herein defined. The process of this invention produces realizable ethanol at high selectivity and rate by the homologation of methanol with synthesis gas at relatively milder reaction conditions than one normally expects to be required.

DETAILED DESCRIPTION OF THE INVENTION

In the reaction of synthesis gas alone or in mixtures with other organic compounds there are several criteria required of the catalyst systems. The systems must be as stable as possible under the reaction conditions so as to maintain the reaction, they should have a high selectivity for the desired product, and they should have a high rate of formation of the desired product.

Stability of the catalyst relates to how long the catalyst system remains active or functional before either breaking down or losing its catalytic effectiveness. The most desirable catalyst is one which does not lose its catalytic activity and can be recycled time and time again.

Selectivity relates to the ability of the catalyst to preferentially produce a high or large quantity of the desired product in preference to other products. The selectivity determined by gas chromatographic analysis of the reaction product recovered and is expressed in this application as the area percent or mole percent of realizable alkanol produced and is based on the total amount of realizable alkanol formed.

Rate of formation, or rate, relates to the amount of alkanol charged to the reactor that is converted to realizable alkanol per unit of time. It is expressed in moles per liter per hour.

Realizable alkanol or realizable alcohol is the amount of the next higher alkanol homologue formed plus the amounts of by-products formed that upon recycle will form such higher alkanol homologue. Thus, for example, in the homologation of methanol charged to the reactor one generally recovers a reaction product mixture containing ethanol, acetaldehyde, ethyl acetate, dimethyl acetal, diethyl ether, methyl acetate, acetic acid, dimethyl ether, methyl ethyl ether and unreacted methanol and methyl iodide. The realizable ethanol is based on the amount of ethanol, and the ethanol equivalents available from the acetaldehyde, ethyl acetate, dimethyl acetal, diethyl ether, and methyl ethyl ether present.

Conversion is the amount of initially charged alkanol that is homologated during the reaction to realizable alkanol.

The desired goal is high values for all of the above and continued efforts are being made to find new processes and systems to reach this goal without having a significant detrimental effect on the overall process. The prior art has evolved with this in mind and, though many processes and systems are effective, improvement is always desirable.

The present invention is based on the unexpected and unpredictable discovery of a process using a rhodium-based homologation catalyst that selectively generates ethanol. This process employs a catalyst system containing rhodium atom, ruthenium atom, iodine atom and a bis(diorganophosphino) alkane ligand of the general formula:

This catalyst system allows the methanol homologation reaction to be carried out at operating pressures that can be below 1,000 psig while achieving realizable ethanol rates and selectivities approaching the best heretofore reported in the literature with cobalt catalysts at pressures of 4,000 to 8,000 psig. The use of reduced reaction pressure possible in the process of this invention is a significant and major breakthrough in methanol homologation technology. Generally the catalyst system is a soluble homogeneous system; however, one can, if desired, deposit the catalyst on an inert support to give a heterogeneous system. Both of these techniques are known to one of ordinary skill in the art. This unexpected homologation reaction process requires the use of the defined ligand. In the absence of the ligand realizable ethanol rates and selectivities are negligible. As shown by Comparative Experiment A the reaction could not be sustained for any significant period of time and selectivity to realizable ethanol was insignificant. The combination of this ligand with the stated metal atoms provides, to the best of our knowledge, the first reported rhodium-based homologation catalyst. Applicant has shown it readily produces ethanol from methanol and synthesis gas at high selectivity, conversion and rate. The use of rhodium-based catalysts for the homologation of methanol to ethanol is neither suggested nor to be expected or predicted from the published prior art. The prior art teaches that the rhodium-based catalyzed reaction of methanol with synthesis gas causes carbonylation reactions and selective formation of esters and acids as the primary products, not alkanols.

The values achieved in the homologation of methanol to ethanol by the process of this invention at temperatures below about 150° C. and pressures below 2,500 psig, e.g., at about 1,000 psig, approach the best values reported for the known standard Co-Ru-I catalysts that require operating conditions of 180° C. to 200° C. and pressures of 4,000 psig to 6,000 psig. The reduction in temperature and pressure made possible by the rhodium-based catalyzed process of this invention is probably the first major improvement in homologation technology since the introduction of iodine promoters about three decades ago.

In the process of the present invention an alkanol R'OH is reacted with synthesis gas using a catalyst system containing rhodium atoms, ruthenium atoms, iodine atoms and the ligand $R_2PXPR_2$. At mild operating conditions, this process produces the next higher alkanol homologue at higher realizable ethanol selectivity and higher rate than obtained with other catalysts.

In the alcohol or alkanol formula R' is a monovalent hydrocarbyl group, preferably an alkyl group. It can be an alkyl group having from 1 to about 20 carbon atoms, preferably 1 to about 10 carbon atoms, and most preferably from 1 to 4 carbon atoms; an aklenyl group having from 2 to about 20 carbon atoms, preferably 2 to about 10 carbon atoms, and most preferably from 2 to 4 carbon atoms; or an aralkyl in which the aryl moiety is phenyl or naphthyl and the alkyl moiety contains from 1 to about 10 carbon atoms, preferably 1 to 4 carbon atoms. The R' group can be linear or branched and it can be unsubstituted or substituted with groups which will not have an adverse effect on the homologation reaction; further, the alkenyl groups can have more than a single unsaturated bond. Among the preferred alcohols are methanol, ethanol, the propanols and the butanols; the most preferred are methanol nd ethanol.

As the rhodium atom component one can use a single rhodium compound or a mixture of two or more rhodium compounds. The rhodium component of the catalyst system can be supplied from any number of sources, many of these are known to those of ordinary skill in the art. Thus, it is not necessary for an understanding thereof to specifically enumerate every suitable type and every specific compound since any of the known rhodium compounds can be used.

The rhodium component of the catalyst system of the present invention may be provided by introducing into the reaction zone a compound of rhodium or may be provided by introducing into the reaction zone rhodium. Among the materials which may be charged to the reaction zone to provide the rhodium component of the catalyst system of the present invention are rhodium metal, rhodium salts and oxides, organo rhodium compounds, coordination compounds of rhodium, and the like. Specific examples of materials capable of providing the rhodium constituent of the catalyst system of the present invention may be taken from the following non-limiting partial list of suitable materials.

$RhCl_2$
$RhBr_3$
$RhI_3 \cdot 3H_2O$
$RhCl_3 \cdot 3H_2O$
$RhBr_3 \cdot 3H_2O$
$Rh_2(CO)_4Cl_2$
$Rh_2(CO)_4Br_2$
$Rh_2(CO)_4I_2$
$Rh_2(CO)_8$
$Rh[(C_6H_5)_3P]_2(CO)I$
$Rh[(C_6H_5)_3P]_2(CO)Cl$
Rh metal
$Rh(NO_3)_3$
$Rh(CO)_2$ acac
$Rh(SnCl_3)[(C_6H_5)_3P]_2$
$RhCl(CO)[C_4H_5)_3As]_2$
$RhI(CO)[(C_6H_5)_3Sb]_2$
$[(n-C_2H_9)_4N][Rh(CO)_2X_2]$ where X=Cl—, Br—, I—
$[(n-C_4H_9)_4As][Rh(CO)_2X_4]$ where X=Cl—, I—
$[(n-C_4H_9)_4P][Rh(CO)I_4]$
$Rh[(C_6H_5)_3P]_2(CO)Br$
$Rh[(n-C_4H_9)_3P]_2(CO)Br$
$Rh[(n-C_4H_9)_3P]_2(CO)I$
$RhBr[(C_6H_5)_3P]_3$
$RhI[(C_6H_5)_3P]_3$
$RhCl[(C_6H_5)_3P]_2$
$RhCl[(C_6H_5)_3P]_3H_2$
$[(C_6H_5)_3P]_3Rh(CO)H$
$Rh_2O_3$
$[Rh(C_3H_4)_2Cl]_2$
$K_4Rh_2Cl_2(SnCl_2)_4$
$K_4Rh_2Br_2(SnBr_3)_4$
$K_4(Rh_2I_2)_4$
$Rh[R_2PXPR_2]_{1\ or\ 2}Z$ in which Z is any suitable counterion Among the preferred rhodium compounds are those which react with the bis(diorganophosphino) alkane ligand to form a rhodium-phosphine complex. These complexes are generally formed when the coponents are initially charged to the reactor, or the complexes can be preformed and charged to the reactor. In addition, one may form complexes containing rhodium, ruthenium and the bis(diorganophosphino) alkane when the components are charged to the reactor, or these complexes can be preformed and then charged to the reactor. Further, any of the above complexes may be formed during the course of the reaction. Further, any of the known rhodium complexes or rhodium-ruthenium compounds or complexes can be used.

As the ruthenium atom component one can use a single ruthenium compound or a mixture of two or more ruthenium compounds. The ruthenium compounds are well known to those of ordinary skill in this art. Illustrative of such ruthenium compounds one can name ruthenium trichloride, ruthenium tribromide, ruthenium triiodide, ruthenium acetate, ruthenium acetylacetonate, ruthenium propionate, ruthenium octanoate, ruthenium dioxide, ruthenium tetraoxide, ruthenium pentacarbonyl, triruthenium dodecarbonyl and the like. Convenient sources of ruthenium are ruthenium trichloride and triruthenium dodecacarbonyl.

Also useful are those compounds that contain both the rhodium and ruthenium atoms in the same molecule. They can be used alone or in combination with the previously described rhodium and ruthenium compounds.

The halide component of the catalyst can be a halogen compound containing iodine, bromine or chlorine or two or more of the same, or the elemental halogen per se, or any mixtures of compounds and/or elements. Their identities are well known to those of ordinary skill in this art. The preferred halogen compound is iodine or the inorganic or organic compounds containing the iodine atom. As indicated, the suitable halogen compounds are well known to those of average skill in this art and a complete listing is not necessary for their comprehension. Illustrative thereof one can mention barium iodide, hydriodic acid, cobalt iodide, Potassium iodide, lithium iodide, sodium iodide, calcium iodide, ammonium iodide, methyl iodide, ethyl iodide, propyl iodide, 2-ethylhexyl iodide, n-decyl iodide, acetyl iodide, propionyl iodide; the organic ammonium iodides of the formula R'''$_4$NI and the organic phosphonium iodides of the formula R'''$_4$PI in which R''' is alkyl, saturated or unsaturated, substituted or unsubstituted, having from 1 to about 10 carbon atoms or aryl, unsubstituted or substituted, having from 6 to 10 ring carbon atoms such as trimethyl ammonium iodide, tetraethyl ammonium iodide, tetra-2-ethylhexyl ammonium iodide, tetraphenyl ammonium iodide, tetramethyl phosphonium iodide, tetraphopylphosphonium iodide, tetra-2-ethylhexyl phosphonium iodide, tetrapropyl phosphonium iodide, tetra-2-ethylhexyl phosphonium iodide, methyltriphenyl phosphonium iodide, and the like; methylammonium iodide, tri-p-tolyl-ammonium iodide, decylammonium iodide, ethylphosphonium iodide, triphenylphosphonium iodide, tricyclohexylphosphonium iodide, tri-p-tolyphosphonium iodide, and the like; also useful are bromine and its corresponding compounds and chlorine and its corresponding compounds. Any source of halogen atom can be used provided that it does not have a deleterious effect on the reaction. The preferred source of the iodine atom is methyl iodide.

The bis(diorganophosphino) alkane ligand is represented by the general formula:

wherein X is a linear or branched alkyl or alkenyl or cyclic bridging divalent group having from 1 to 10 carbon atoms between the two P atoms, preferably 2 to about 6 carbon atoms, most preferably 3, and can be unsubstituted or substituted with any group that does not significantly detract from the catalytic activity of the reaction (e.g. phenyl, nitro, halogen, alkyl, alkaryl, aralkyl) and R is (i) a hydrogen atom with the proviso that not more than one hydrogen atom is attached to a P atom, or (ii) an alkyl group having from 1 to about 10 carbon atoms preferably 2 to about 5 carbon atoms, it can be linear or branched, or (iii) an aryl, aralkyl or alkaryl group having 6 or 10 carbon atoms in the aryl moiety (phenyl, naphthyl) and from 1 to about 10 carbon atoms in the alk-moiety, preferably 1 to 3 carbon atoms. The R radicals can be the same or different. A preferred ligand is bis(diphenylphosphino)propane.

Illustrative of suitable bis(diorganophosphino)alkane ligands one can mention bis(diphenylphosphino)methane, 1,3-bis(diphenylphosphino)propane, 1,10-bis(diphenylphosphino)decane, 1,3-bis(diethylphosphino)propane, 1,3-bis(ethyl phenylphosphino)propane, 1,4-bis(diphenylphosphino)butane, 1,3-bis(dipropylphosphino)propane, 1-diethylphosphino-3-dipropylphosphino propane, 1,3-bis(diphenylphosphino)-2-methylpropane, 1,3-bis(diphenylphosphino)-1-butylpropane, 1-diamylphosphino-3-diphenylphosphino-1,3-diethylpropane, 1,3-bis(diphenylphosphino)-2,2-dimethylpropane, 1,2-bis(diphenylphosphino)propane, 1,2-bis(diphenylphosphino)benzene, and the like.

One can optionally have present as a secondary ligand any of the other known organic ligands in small amounts. The presence of these other known or secondary ligands is not required but the presence of the bis(diorganophosphino)alkane is. As used in this application the term "secondary ligand" denotes any of the known ligands other than the R$_2$PXPR$_2$ ligands herein defined that are useful in the homologation reaction. These secondary ligands are well known in the art and any of these can be used provided they do not have an adverse effect on the reaction. Among those of particular utility are the tertiary amines and the tri- and pentavalent phosphorus compounds. Though those skilled in the art know these compounds, illustrative of suitable compounds one can mention triethylphosphine, tributylphosphine, tri-2-ethylhexylphosphine, triphenylphosphine, tri(4-methoxyphenyl)phosphine, tri-p-tolylphosphine, tri(3-chlorophenyl)phosphine, diphenyl hexylphosphine, dimethyl (3-methoxyphenyl)phosphine, dibutyl stearylphosphine, tribenzylphosphine, dipropyl phenylphosphine, ethyl dipropylphosphine, tricyclohexylphosphine, cyclohexyl dibutylphosphine, propyl diphenylphosphine, dipropyl phenylphosphine, phenyl diethylphosphine, tridecylphosphine, trioctadecylphosphine, tribenzylphosphine, methyl diethylphosphine, ethyl diphenylphosphine, tolyl diethylphosphine, cyclohexyl diethylphosphine, diethyl cyclohexylphosphine, trimethylamine, triethylamine, tri-n-butylamine, tri-t-butylamine, tri-2-ethylhexylamine, methyl dibutylamine, tridodecylamine, tristearylamine, ethyl dibutylamine, tricyclohexylamine, triphenylamine, tri(4-methoxyphenyl)amine, tri(p-chloropenyl)amine, dibutyl phenylamine, dipentyl cyclopentylamine, ethyl diphenylamine, trinaphthylamine, tri-p-tolylamine, tri-benzylamine, tri(3-methylcylohexyl)amine, and the arsines, stibines and bismuthines corresponding to the above-identified phosphines and amines. These and many others are known in the art. They can be used singly or, if one desires, mixtures containing two or more ligands can be used. One can also employ a phosphine oxide or phosphite corresponding to the above phosphines as the ligand; these are also well known.

In addition, a solvent which does not interfere with the reaction can be optionally be present. Many solvents are known as useful in the homologation reaction. They are essentially inert and should not interfere with the reaction to any significant extent. Illustrative thereof one can mention 1,4-dioxane, the polyethylene glycol diethers or esters, diphenyl ether, sulfolane, toluene, and the like. The reaction is preferably carried out in the absence of any solvent or diluent other than those required to introduce reactants or catalyst components.

The rhodium atom concentration can vary over a wide range. A catalytic amount of rhodium sufficient to catalyze the homologation reaction must be present. The molar ratio of rhodium to alcohol can vary from 1:25 to 1:2,500, the preferred range is from about 1:50 to about 1:1,500, with the most preferred range being from about 1:100 to about 1:1,000.

The mole ratio of Rh atom:Ru atom can vary from about 1:10 to about 10:1, preferably from about 6:1 to about 1:6 and most preferably from about 3:1 to about 1:3.

The Rh:I mole ratio can very from about 1:500 to about 500:1, preferably from about 1:300 to about 300:1 and most preferably from about 1:100 to about 100:1.

The Rh:R$_2$PXPR$_2$ mole ratio can vary from 1:100 to 100:1, preferably from 10:1 to about 1:10 and most preferably from about 2:1 to about 1:2.

The reaction is carried out at a temperature of from about 50° C. to about 250° C., or higher, preferably from about 100° C. to about 175° C. and most preferably from about 110° C. to about 160° C.

The pressure of the reaction can be from about 100 psig to about 10,000 psig, preferably from about 250 psig to about 5,000 psig and most preferably from about 500 psig to about 2,500 psig.

The mole ratio of $H_2$:CO in the synthesis gas mixture can range from about 1:10 to 10:1, preferably from about 1:5 to 5:1.

The reaction time varies depending upon the reaction parameters, reactor size and charge, and the individual components used and specific process conditions employed. The reaction can be a batch or continuous process reaction.

When the process is carried out as described in this specification conversion rates of realizable ethanol approaching 4 moles per liter per hour and selectivities to realizable ethanol approaching 85% are attainable in the homologation of methanol to ethanol at lower temperature and pressure conditions than were heretofore required to attain such values. In all of the reactions the rhodium component, the ligand and the methanol were initially charged to the reactor under nitrogen and stirred for about five minutes. The ruthenium component and methyl iodide were then added. In this manner pre-coordination of the rhodium and the phosphorus ligand is achieved.

The examples and experiments of Examples 1 to 8 were performed in a 100 mL Hastelloy ® autoclave that was equipped with temperature and pressure sensing means, heating and cooling means, magnedrive agitator means, and inlet and outlet means for introducing and removing components from the reactor. Autoclaves used in synthesis gas reactions are well known in the art and they can be used in this process.

The autoclave was cleaned prior to each experiment by washing with methanol at about 100° C. under a synthesis gas pressure of about 500 to 1000 psig with agitation for about 30 minutes. The autoclave was drained, rinsed with dry acetone and dried with nitrogen.

The cleaned autoclave was charged with the liquid components followed by any solid components, sealed and pressured to 400 psig with synthesis gas of the desired composition. The reactor was maintained at 400 psig for 10 minutes to check for leaks. The autoclave contents were then heated to the selected temperature, with agitation, and pressured with the synthesis gas to 25 psig above the desired specified pressure. The reaction was allowed to consume synthesis gas until the pressure had fallen to 25 psig below the desired pressure. The pressure was maintained within plus or minus 25 psig of the operating pressure by repressurizing with synthesis gas as necessary. One such cycle is considered 50 psig gas uptake or consumption.

At the end of a run the reactor was cooled to 20° C., the pressure was vented and the liquid products were collected in a chilled pressure bottle equipped with a septum seal. The reactor was solvent-washed until the rinses appeared clean.

Analysis of the liquid products was carried out using a Varian: Model 3700 capillary gas chromatograph equipped with a FID detector and a Durabond 1701 30 m by 0.32 mm capillary column.

The following examples serve to further illustrate this invention. In the examples the data is reported in terms of area percent or mole percent, unless otherwise indicated.

EXAMPLE 1

The autoclave was charged with 0.52 g of rhodium dicarbonyl acetylacetonate, $Rh(CO)_2$ acac, (2 mmol), 0.82 g of ruthenium trichloride hydrate, 0.82 g of 1,3-bis(diphenylphosphino)propane (2 mmol), 2.5 mL of methyl iodide (40.1 mmol) and 40 mL of methanol. Following the procedure described above the reactor contents was heated to 140° C. and the pressure was adjusted to 1,000 psig using a $H_2$:CO mixture having a 2:1 mole ratio. The reaction was continued for 2.75 hours at 975±25 psig, during which period 3,350 psig of synthesis gas was consumed, and then arbitrarily stopped. The reactor was then cooled and the products recovered as described above. Analysis of the recovered liquid product indicated formation and presence of the following compounds:

|  | Area Percent |
|---|---|
| Ethanol | 27.5% |
| Acetaldehyde | 10.1% |
| Ethyl acetate | 10.2% |
| Methyl acetate | 11.5% |
| Acetic acid | 2.5% |
| Dimethyl acetal | 0.5% |
| Diethyl ether | 1.7% |
| Dimethyl ether | 11.9% |
| Methanol | 17.5% |
| Methyl iodide | 2.9% |

The selectivity to realizable ethanol was 70.41% and the rate of formation of realizable ethanol was 3.3 moles per liter per hour.

The example shows that the homogeneous catalyst system containing rhodium atom, ruthenium atom, iodide atom and bis(diorganophosphino)alkane ligand [i.e., bis(diphenylphosphino)propane] selectively generates realizable ethanol under mild reaction conditions at a high rate.

EXAMPLE 2

The reaction was carried out essentially the same as described in Example 1 except that 1.64 g of 1,3-bis(diphenylphosphino)propane (4 mmol) was used. The reaction consumed 3,663 psig of synthesis gas in 3.15 hours and was then arbitrarily stopped. Analysis of the recovered liquid product indicated formation and presence of the following compounds:

|  | Area Percent |
|---|---|
| Ethanol | 29.0% |
| Acetaldehyde | 9.5% |
| Ethyl acetate | 9.0% |
| Methyl acetate | 10.0% |
| Acetic acid | 2.7% |
| Dimethyl acetal | 0.5% |
| Diethyl ether | 2.0% |
| Dimethyl ether | 11.0% |
| Methanol | 17.88% |
| Methyl iodide | 2.5% |

The selectivity to realizable ethanol was 72.73%.

Comparative Experiment A

For comparative purposes the reaction was carried out as described in Examples 1 and 2 except the ligand 1,3-bis(diphenylphosphino)propane was not present.

The reaction consumed 771 psig of synthesis gas in 0.6 hour at which time the reaction died and there was no further evidence of synthesis gas consumption. This experiment shows the presence of the bis(dialkyl-phosphino)alkane ligand is critical for a sustained reaction and in its absence little, if any, ethanol is formed. Analysis of the recovered liquid product indicated formation and presence of the following compounds:

| | Area Percent |
|---|---|
| Ethanol | 1.07% |
| Acetaldehyde | 1.07% |
| Ethyl acetate | 0.61% |
| Methyl acetate | 35.40% |
| Acetic acid | 4.90% |
| Dimethyl acetal | 0.91% |
| Dimethyl ether | 12.89% |
| Diethyl ether | 1.15% |
| Methanol | 34.98% |
| Methyl iodide | 4.27% |

Selectivity to realizable ethanol was only 8.99%.

EXAMPLE 3

The reaction was carried out at 130° C. under conditions essentially identical to Example 1. The materials originally charged to the reactor were 0.52 g of rhodium dicarbonyl acetylacetonate (2 mmol), 1.64 g of ruthenium trichloride hydrate, 1.64 g of 1,3-bis(diphenylphosphino)propane (4 mmol), 2.5 mL of methyl iodide (40.1 mmol) and 40 mL of methanol. The reaction consumed 3,038 psig of synthesis gas in 4.5 hours and was then arbitrarily stopped. Analysis of the recovered liquid product indicated formation and presence of the following compounds:

| | Area Percent |
|---|---|
| Ethanol | 34.0% |
| Acetaldehyde | 9.0% |
| Ethyl acetate | 6.3% |
| Methyl acetate | 8.0% |
| Acetic acid | 1.0% |
| Dimethyl acetal | 0.3% |
| Diethyl ether | 2.0% |
| Dimethyl ether | 11.0% |
| Methanol | 24.0% |
| Methyl iodide | 1.8% |

The selectivity to realizable ethanol was 80.1% and the rate of formation of realizable ethanol was 2.5 moles per liter per hour.

EXAMPLE 4

The reaction was carried out under essentially the same conditions described in Example 3. The materials originally charged to the reactor were 1.95 g (2 mmol) of the complex of one mole of rhodium monochloride with two moles of 1,3-bis(diphenylphosphino)propane of the formula Rh[1,3-bis(diphenylphosphino)propane]$_2$Cl, 1.23 g of ruthenium trichloride hydrate, 2.5 mL of methyl iodide (40.1 mmol) and 40 mL of methanol. The reaction consumed 4,064 psig of synthesis gas in 3.65 hours and was then arbitrarily stopped. Analysis of the recovered liquid product indicated formation and presence of the following compounds:

| | Area Percent |
|---|---|
| Ethanol | 34.1% |
| Acetaldehyde | 13.2% |
| Ethyl acetate | 11.3% |
| Methyl acetate | 6.6% |
| Acetic acid | 3.2% |
| Diethyl ether | 1.07% |
| Dimethyl ether | 10.4% |
| Methanol | 10.9% |
| Methyl iodide | 2.01% |

The selectivity to realizable ethanol was 80.4% and the rate of formation of realizable ethanol was 3.2 moles per liter per hour.

EXAMPLE 5

The reaction was carried out under essentially the same conditions described in Example 1. The materials originally charged to the reactor were 0.52 g of rhodium dicarbonyl acetylacetonate (2 mmol), 0.82 g of ruthenium trichloride hydrate, 0.95 g of 1,3-bis(isobutylphenylphosphino)propane (2.5 mmol), 2.5 mL of methyl iodide (40.1 mmol) and 40 mL of methanol. The reaction consumed 1,600 psig of synthesis gas in 2 hours and was then arbitrarily stopped. Analysis of the recovered liquid product indicated formation and presence of the following compounds:

| | Area Percent |
|---|---|
| Ethanol | 16.5% |
| Acetaldehyde | 7.21% |
| Ethyl acetate | 5.6% |
| Methyl acetate | 11.1% |
| Acetic acid | 1.3% |
| Dimethyl acetal | 3.9% |
| Diethyl ether | 0.4% |
| Dimethyl ether | 12.5% |
| Methanol | 27.4% |
| Methyl iodide | 3.35% |

The selectivity to realizable ethanol was 63%.

EXAMPLE 6

A series was carried out to evaluate the effect of the length of the —X— group in the R$_2$PXPR$_2$ ligand. The reactions were carried out similarly to Example 1 except runs A and B employed H$_2$:CO=1:1. The reaction time, psig synthesis gas consumed, catalyst composition, and selectivity to realizable ethanol is summarized in Table I.

TABLE I

| Run | Ligand(L) | Rh:Ru:L:CH$_3$I | Time (hr) | Gas Uptake (psi) | ETOH Sel., % |
|---|---|---|---|---|---|
| a | Ph$_2$PCH$_2$PPh$_2$ | 1:1:1:10 | 2.25 | 615 | 11.6 |
| b | Ph$_3$P | 1:1:1:20 | 0.25 | 500 | 6.3 |
| c | Ph$_2$PCH$_2$CH$_2$PPh$_2$ | 1:2:2:20 | 1.5 | 620 | 43.3 |
| d | Cy$_2$PCH$_2$CH$_2$PCy$_2$ | 1:2:2:20 | 1.0 | 300 | 3.6 |
| e | (p-CH$_3$Ph)$_2$PCH$_2$CH$_2$P(p-CH$_3$Ph)$_2$ | 1:2:2:20 | 1.4 | 490 | 26.2 |
| f | Ph$_2$PCH$_2$CH$_2$CH$_2$CH$_2$PPh$_2$ | 1:2:2:20 | 1.0 | 300 | 6.6 |

All Runs: 140° C., 975 psig. Ph = phenyl and Cy = cyclohexyl.

EXAMPLE 7

In this series the $H_2$:CO mole ratio was 2:1. In this group variation of the Rh:Ru:ligand mole ratio was examined. The reactions were carried out as described in Example 1. Table II summarizes the reactant ratios, and reaction times and gas consumption or uptake and Table III summarizes, in area percent, the analysis of the compounds in the liquid product and selectivity to realizable ethanol and to other oxygenates. In all instances the mole ratios of materials charged were based on an initial charge of 2 mmol of $Rh(CO)_2$ acac; 40 mL of methanol was initially charged.

The data show that in the absence of ligand ethanol selectivity is very low; some metal components precipitation was also noted. Comparison of Runs (b) and (c) shows an increase in selectivity to realizable ethanol and a 3.5 fold increase in gas uptake when the Ru concentration was doubled. It was also noted best results were generally obtained at a Rh:$CH_3I$ molar ratio of 1:20.

TABLE II

| Run | Molar Ratio | | | | Time | Uptake |
|---|---|---|---|---|---|---|
| | Rh | Ru | L | $CH_3I$ | hr | psig |
| Comp. Exp. A | 1 | 1 | 0 | 20 | 0.6 | 771 |
| Comp. Exp. B | 1 | 2 | 0 | 20 | 0.75 | 926 |
| a | 1 | 2 | 0.5 | 20 | 0.63 | 694 |
| b | 1 | 1 | 1 | 20 | 1.22 | 950 |
| c | 1 | 2 | 1 | 20 | 2.8 | 3350 |
| d | 1 | 2 | 2 | 20 | 3.2 | 3663 |
| e | 1 | 2 | 2 | 40 | 1.5 | 1277 |
| f | 1 | 2 | 1 | 10 | 1.0 | 1198 |
| g | 1 | 2 | 1 | 40 | 0.62 | 538 |
| h | 1 | 3 | 1 | 20 | 1.83 | 2777 |
| i | 1 | 3 | 2 | 20 | 2.0 | 2540 |
| j | 1 | 3 | 3 | 20 | 2.2 | 2422 |
| k | 1 | 3 | 3 | 40 | 3.25 | 2250 |

L = 1,3-bis(diphenylphosphino)propane
Runs (c) and (d) are Examples 1 and 2, respectively.

TABLE III

| Run | Comp A | Comp C | a | b | c | d | e | f | g | h | i | j | k |
|---|---|---|---|---|---|---|---|---|---|---|---|---|---|
| Compounds, Area % | | | | | | | | | | | | | |
| Ethanol | 1.07 | 2.28 | 3.84 | 8.2 | 27.5 | 29.0 | 6.1 | 13.3 | 2.9 | 24.0 | 26.8 | 29.4 | 41.7 |
| Acetaldehyde | 1.07 | 1.22 | 3.35 | 2.3 | 10.1 | 9.5 | 1.6 | 4.47 | 3.41 | 8.2 | 8.42 | 6.6 | 1.7 |
| Ethyl acetate | 0.61 | 0.97 | 0.56 | 1.5 | 10.2 | 9.0 | 1.99 | 2.25 | 0.6 | 7.2 | 6.2 | 5.82 | 7.5 |
| Methyl acetate | 35.40 | 29.24 | 14.26 | 12.0 | 11.5 | 10.0 | 19.86 | 16.1 | 15.27 | 14.8 | 12.1 | 12.4 | 10.8 |
| Acetate acid | 4.90 | 2.98 | 0.91 | 1.0 | 2.5 | 2.7 | 2.55 | 1.2 | 1.49 | 3.0 | 2.2 | 1.4 | 5.1 |
| Dimethyl acetal | 0.91 | 2.00 | 2.73 | 6.5 | 0.5 | 0.5 | 1.21 | 1.0 | 1.6 | 0.33 | 0.4 | 0.1 | 0 |
| Diethyl ether | 12.89 | 1.65 | 0.35 | 1.0 | 1.7 | 2.0 | 0.6 | 1.6 | 0.8 | 1.39 | 1.4 | 1.0 | 0.1 |
| Dimethyl ether | 1.15 | 9.60 | 9.10 | 10.3 | 11.9 | 11.8 | 12.3 | 6.15 | 12.05 | 10.0 | 9.5 | 9.0 | 0.08 |
| Methanol | 34.98 | 40.95 | 58.82 | 47.3 | 17.5 | 17.88 | 32.3 | 48.04 | 48.55 | 24.8 | 28.3 | 29.2 | 29.4 |
| Methyl iodide | 4.27 | 4.18 | 4.22 | 4.1 | 2.9 | 2.5 | 7.04 | 1.26 | 8.5 | 3.0 | 1.9 | 1.4 | 0.4 |
| Selectivity, Area % | | | | | | | | | | | | | |
| Realizable ethanol | 8.99 | 16.44 | 35.20 | 47.48 | 70.41 | 72.73 | 29.36 | 52.77 | 31.46 | 63.88 | 69.82 | 70.86 | 71.08 |
| Other oxygenates | 91.01 | 83.56 | 64.80 | 52.52 | 25.59 | 27.27 | 70.64 | 47.23 | 68.54 | 36.12 | 30.18 | 29.14 | 28.92 |

EXAMPLE 8

The effect of variation in temperature was studied. The reactions were carried out as described in Example 7. Table IV summarizes the reaction temperatures employed, the reactant ratios and other reaction conditions and Table V summarizes, in weight percent, the results achieved. The data show that realizable ethanol selectivity increases as the temperature decreases.

TABLE IV

| Run | Molar Ratio | | | | Temp °C. | Time hr | Uptake psig |
|---|---|---|---|---|---|---|---|
| | Rh | Ru | L | $CH_3I$ | | | |
| a | 1 | 1 | 1 | 20 | 155 | 0.55 | 617 |
| b | 1 | 1 | 1 | 20 | 140 | 1.22 | 950 |
| c | 1 | 3 | 2 | 20 | 150 | 1.0 | 2436 |
| d | 1 | 3 | 2 | 20 | 140 | 2.0 | 2540 |
| e | 1 | 3 | 2 | 20 | 130 | 4.5 | 3038 |

L = bis(diphenylphosphino)propane
Run b = Example 7b;
Run d = Example 7i;
Run e = Example 3.

TABLE V

| Run | a | b | c | d | e |
|---|---|---|---|---|---|
| Compounds, Area % | | | | | |
| Ethanol | 3.86 | 8.2 | 17.4 | 26.8 | 34.0 |
| Acetaldehyde | 2.84 | 2.3 | 6.2 | 8.42 | 9.0 |
| Ethyl acetate | 0.58 | 1.5 | 6.6 | 6.2 | 6.3 |
| Methyl acetate | 11.7 | 12.0 | 19.3 | 12.1 | 8.0 |
| Acetic acid | 1.08 | 1.0 | 3.3 | 2.2 | 1.0 |
| Dimethyl acetal | 7.2 | 6.5 | 1.7 | 2.2 | 1.0 |
| Diethyl ether | 1.14 | 1.0 | 2.1 | 1.4 | 2.0 |
| Dimethyl ether | 11.4 | 10.3 | 9.7 | 9.5 | 11.0 |
| Methanol | 50.34 | 47.3 | 24.0 | 28.3 | 24.0 |
| Methyl iodide | 4.09 | 4.1 | 2.75 | 1.9 | 1.8 |
| Selectivity | | | | | |
| Realizable ethanol | 40.88 | 47.48 | 53.1 | 69.82 | 80.11 |
| Other oxygenates | 59.12 | 52.52 | 46.8 | 30.18 | 19.89 |

EXAMPLE 9

The experiments of Example 9 were performed in a 300 mL Hastelloy: magnadrive autoclave that was treated in the same manner as the smaller autoclave. In these experiments the procedure followed was essentially the same using synthesis gas having a $H_2$:CO mole ratio of 2:1 and 150 ml of methanol charge and the pressure was maintained to within 200 psig by repressurizing as necessary. All experiments were run for three hours. After completion of the run the reactor was cooled to below 20° C. and a gas sample was taken; the reactor was slowly vented and the product collected in a crown-capped bottle at 0° C. Gas analyses we·e performed on a Carle Analytical Gas Chromatograph, Series S. Liquid products were analyzed using a Hewlett-Packard HP5890A gas chromatograph equipped with a DB 1701 30 m by 0.32 mm capillary column attached to a flame ionization detector. Products were quantified using acetonitrile as the internal standard. The reactants, reaction conditions and results are summarized in Table VI. The ligand used was 1,3-bis(diphenylphosphino)propane.

TABLE VI

| Run | a | b | c | d | e | f | g | h | i | j | k | l |
|---|---|---|---|---|---|---|---|---|---|---|---|---|
| Rh(CO)$_2$ acac, mmol | 2 | 2 | 2 | 2 | 2 | 2 | 2 | 2 | 2 | 2 | 2 | 2 |
| RuCl$_3$*, mmol | 2 | 2 | 2 | 2 | 2 | 4 | 6 | 6 | 6 | 6 | 6 | 6 |
| Ligand, mmol | 2 | 2 | 6 | 6 | 6 | 4 | 2 | 2 | 6 | 6 | 6 | 6 |
| CH$_3$I, mmol | 40 | 80 | 80 | 80 | 40 | 60 | 80 | 40 | 40 | 80 | 40 | 40 |
| Temp., °C. | 125 | 140 | 125 | 125 | 140 | 132 | 125 | 140 | 125 | 140 | 155 | 140 |
| Uptake, psig | 2400 | 3500 | 1510 | 1550 | 3420 | 3570 | 3150 | 5770 | 2550 | 5050 | 1580 | 5430 |
| Compounds, wt % | | | | | | | | | | | | |
| Ethanol | 2.95 | 7.15 | 1.06 | 0.62 | 4.75 | 7.95 | 5.46 | 14.12 | 3.47 | 11.17 | 2.78 | 12.97 |
| Acetaldehyde | 2.34 | 3.12 | 0.54 | 0.48 | 1.35 | 2.03 | 1.11 | 3.30 | 1.12 | 2.50 | 2.27 | 3.15 |
| Ethyl acetate | 0.03 | 0.19 | Trace | 0.0 | 0.13 | 0.16 | 0.16 | 0.94 | 0.06 | 0.61 | 0.14 | 0.85 |
| Methyl acetate | 1.27 | 2.10 | 1.10 | 1.58 | 2.42 | 1.98 | 2.62 | 4.95 | 1.96 | 3.57 | 4.69 | 6.07 |
| Acetic acid | 0.0 | 0.31 | 0.0 | Trace | 0.0 | 0.46 | 0.24 | 0.93 | 0.0 | 0.79 | 0.62 | 0.65 |
| Dimethyl acetal | 10.43 | 4.73 | 10.24 | 10.77 | 11.52 | 7.62 | 5.67 | 0.64 | 9.38 | 3.18 | 3.49 | 2.27 |
| Diethyl ether | 0.0 | 0.06 | Trace | Trace | Trace | Trace | 0.02 | 0.22 | 0.0 | 0.11 | 0.0 | 0.27 |
| Dimethyl ether | 1.99 | 4.73 | 1.36 | 1.42 | 1.60 | 1.44 | 1.11 | 1.79 | 0.79 | 3.01 | 5.73 | 3.15 |
| Methanol | 6.04 | 43.9 | 62.8 | 59.0 | 52.02 | 56.5 | 55.04 | 47.82 | 64.35 | 40.45 | 55.80 | 51.29 |
| CH$_3$I | 2.27 | 4.10 | 2.51 | 2.7 | 1.28 | 1.56 | 2.0 | 0.75 | 0.80 | 2.25 | 1.88 | 1.39 |
| Rate, M/hr. | | | | | | | | | | | | |
| to ethanol | 0.19 | 0.47 | 0.07 | 0.04 | 0.31 | 0.49 | 0.36 | 0.92 | 0.23 | 0.73 | 0.18 | 0.84 |
| to ethanol equivalents | 0.54 | 0.43 | 0.38 | 0.40 | 0.55 | 0.46 | 0.36 | 0.31 | 0.38 | 0.36 | 0.28 | 0.49 |
| to other oxygenates | 0.05 | 0.11 | 0.04 | 0.06 | 0.12 | 0.11 | 0.12 | 0.28 | 0.08 | 0.20 | 0.22 | 0.31 |
| to methane | 0.24 | 0.38 | 0.08 | 0.05 | 0.19 | 0.16 | 0.12 | 0.21 | 0.07 | 0.18 | 0.43 | 0.16 |
| Selectivity, M % | | | | | | | | | | | | |
| Realizable ethanol | 93.1 | 89.2 | 91.1 | 86.9 | 88.0 | 89.7 | 85.3 | 81.5 | 87.9 | 84.2 | 67.5 | 81.3 |
| Other oxygenates | 6.9 | 11.8 | 8.9 | 13.1 | 12.0 | 10.3 | 14.7 | 18.5 | 12.1 | 15.8 | 32.5 | 18.7 |

*as the hydrate

EXAMPLE 10

A series of reactions was carried out at 140° C. as described in Example 9 using synthesis gas having a H$_2$:CO molar ratio of 3:1. The pressures were 2000 psig in Run (a), 1200 psig in Run (b) and 1600 psig in Run (c). It was noted the rate to ethanol and equivalents was lower than a similar run (Run (1) of Example 9) that used 2:1 synthesis gas. It is believed part of the reason for this lower rate may lie in rapid build up of methane. The rate to methane was higher using the higher synthesis gas ratio feed. The three reactions used 2 mmol of rhodium dicarbonylacetylacetonate, 6 mmol of ruthenium trichloride trihydrate, 6 mmol of 1,3-bis(diphenylphosphino) propane and 40 mmol of methyl iodides. The results are summarized in Table VII.

TABLE VII

| Run | a | b | c |
|---|---|---|---|
| Uptake, psig | 3900 | 1360 | 2480 |
| Compound, wt. % | | | |
| Ethanol | 8.47 | 2.90 | 5.52 |
| Acetaldehyde | 3.96 | 1.35 | 2.92 |
| Ethyl acetate | 0.20 | 0.0 | 0.10 |
| Methyl acetate | 2.30 | 1.34 | 2.01 |
| Acetic Acid | 0.0 | 0.0 | 0.0 |
| Dimethyl acetal | 2.04 | 4.52 | 3.43 |
| Diethyl ether | 0.11 | 0.0 | 0.05 |
| Dimethyl ether | 3.70 | 3.04 | 4.10 |
| Methanol | 56.80 | 71.98 | 62.10 |
| Methyl iodide | 1.87 | 1.97 | 2.11 |
| Rate, M/hr. | | | |
| to ethanol | 0.55 | 0.19 | 0.36 |
| to ethanol equivalents | 0.37 | 0.25 | 0.34 |
| to other oxygenates | 0.10 | 0.05 | 0.08 |
| to methane | 0.70 | 0.30 | 0.41 |
| Selectivity, M % | | | |
| Realizable ethanol | 90.3 | 89.2 | 88.9 |
| Other oxygenates | 9.7 | 10.8 | 11.1 |

Though the bis(diorganophosphino)alkanes are known, commercial availability is poor. Therefore, many were made following the published procedures, as shown in the following experimental schemes. The reactions were carried out under dry nitrogen with dry solvents; Cy is cyclohexyl, Ph is phenyl.

Scheme I

Under nitrogen, 10 g of PCy(Ph)$_2$ was placed in a 250 mL round bottom flask followed by 50 mL of degassed CH$_2$Cl$_2$. 1.9 mL of Br(CH$_2$)$_3$Br was slowly added dropwise and the mixture was then refluxed under nitrogen for 11 hours. A $^{31}$P nmr analysis of the product showed incomplete conversion to the desired salt [(Ph)$_2$CyP(CH$_2$)$_3$PCy(Ph)$_2$]Br$_2$. Therefore, the CH$_2$Cl$_2$ was removed by vacuum and 100 mL of benzene added. The mixture was refluxed for 3 hours and $^{31}$P nmr indicated complete conversion to [(Ph)$_2$CyP(CH$_2$)$_3$PCy(Ph)$_2$]Br$_2$.

A 150 mL portion of 30% aqueous sodium hydroxide was added and the mixture was refluxed in air for six hours for complete conversion to (Ph)CyP(O)(CH$_2$)$_3$P(O)Cy(Ph). The dioxide was extracted into CH$_2$Cl$_2$ and this solution was dried over magnesium sulfate and filtered. Triethylamine, 24.5 mL, was added to the dry CH$_2$Cl$_2$ followed by slow addition of 17.5 mL of HSiCl$_3$ in 40 mL of degassed CH$_2$Cl$_2$. The mixture was refluxed for 4 hours, cooled, filtered and solvents removed by vacuum. Then 25 mL CH$_2$Cl$_2$ was added to the resulting material followed by the slow addition of 150 mL of 30% sodium hydroxide with vigorous stirring. The organic layer was separated, dried and after removing the solvent Cy(Ph)P(CH$_2$)$_3$P(Ph)Cy was recovered.

Scheme II

To a 500 mL round bottom flask there was added 400 mL of dry tetrahydrofuran followed by 0.081 mole of HPPh$_2$. The mixture was cooled to 0° C. and 0.081 mole of n-butyl lithium was slowly added to generate LiPPh$_2$; this was slowly warmed to room temperature and stirred for about one hour. The solution was transferred to a dropping funnel and added dropwise to a flask containing 100 mL of 1,3-dichloropropane dissolved in 100 mL of diethyl ether. After stirring overnight the mixture was hydrolyzed with 25 mL of water.

The organic layer was separated and the solvent removed by vacuum to leave $Ph_2P(CH_2)_3Cl$ that was stored under nitrogen until needed.

Following the procedure described above, Cy(Ph)-

M. 1-(n-octylphenylphosphino)-3-diphenylphosphino propane
N. 1-cyclohexylphenylphosphino-3-diphenylphosphino propane.

TABLE VIII

| Run | a | b | c | d | e | f | g | h | i | j | k | l | m | n |
|---|---|---|---|---|---|---|---|---|---|---|---|---|---|---|
| $Rh(CO)_2$ acac, mmol | 2.0 | 2.0 | 2.0 | 2.0 | 2.0 | 2.0 | 2.0 | 2.0 | 2.0 | 2.0 | 2.0 | 2.0 | 2.0 | 2.0 |
| $RuCl_3$*, mmol | 2.0 | 2.0 | 4.0 | 4.0 | 4.0 | 4.0 | 4.0 | 4.0 | 4.0 | 2.0 | 2.0 | 2.0 | 2.0 | 2.0 |
| Ligand | A | B | C | D | E | F | G | H | I | J | K | L | M | N |
| Ligand, mmol | 2.0 | 2.0 | 2.0 | 2.0 | 2.0 | 2.5 | 2.2 | 4.0 | 4.0 | 4.0 | 4.0 | 4.0 | 4.0 | 4.0 |
| $CH_3I$, mmol | 20 | 20 | 20 | 20 | 20 | 20 | 20 | 20 | 20 | 20 | 20 | 20 | 20 | 20 |
| Temp, °C. | 140 | 140 | 140 | 140 | 140 | 140 | 140 | 140 | 140 | 140 | 140 | 140 | 140 | 140 |
| Uptake, psig | 1030 | 170 | 139 | 1040 | 419 | 240 | 1596 | 977 | 1338 | 1900 | 1540 | 1489 | 1543 | 2300 |
| Selectivity, M % | | | | | | | | | | | | | | |
| Realizable ethanol | 35.2 | 25.5 | 34.3 | 13.5 | 24.1 | 9.4 | 64.8 | 17.0 | 54.2 | 71.6 | 60.1 | 58.2 | 59.0 | 68.4 |
| Other Oxygenates | 64.8 | 74.5 | 65.7 | 86.5 | 75.9 | 90.6 | 35.2 | 73.9 | 45.7 | 27.4 | 39.4 | 41.8 | 41.0 | 31.6 |

*as the hydrate

PLi was produced by reacting Cy(Ph)PH with n-butyl lithium. A 27 mmol portion of the $Ph_2P(CH_2)_3Cl$ was dissolved in 100 mL of tetrahydrofuran, cooled to 0° C. and 27 mmol of Cy(Ph)PLi was added dropwise. After stirring overnight the tetrahydrofuran was removed and 100 mL of hexane added. This mixture was refluxed for one hour and filtered hot. The hexane was removed leaving the product $Cy(Ph)P(CH_2)_3PPh_2$.

Following the procedures described in Schemes I and II the following bis(diorganophosphino)propanes were prepared and used in the methanol homologation process of this invention.

Class 1
$R_2P(CH_2)_3PR_2$    R = methyl, ethyl, cyclohexyl, phenyl

Class 2
$R(Ph)P(CH_2)_3P(Ph)R$    R = hydrogen, methyl, ethyl, amyl, cyclohexyl

Class 3
$R_2P(CH_2)_3PPh_2$    R = ethyl, amyl

Class 4
$R(Ph)P(CH_2)_3PPh_2$    R = methyl, n-propyl, n-octyl, cyclohexyl

In the above formulas Ph represents the phenyl group, substituted or unsubstituted.

EXAMPLE 11

The above ligands were used to homologate methanol following the procedure described in Example 1. These reactions are summarized in Table VIII. The ligands are identified as:
A. 1,3-bis(dimethylphosphino)propane
B. 1,3-bis(diethylphosphino)propane
C. 1,3-bis(dicyclohexylphosphino)propane
D. 1,3-bis(phenylphosphino)propane
E. 1,3-bis(methylphenylphosphino)propane
F. 1,3-bis(ethylphenylphosphino)propane
G. 1,3-bis(amylphenylphosphino)propane
H. 1,3-bis(cyclohexylphenylphosphino)propane
I. 1-diethylphosphino-3-diphenylphosphino propane
J. 1-diamylphosphino-3-diphenylphosphino propane
K. 1-methylphenylphosphino)3-diphenylphosphino propane
L. 1-(n-propylphenylphosphino)-3-diphenylphosphino propane

EXAMPLE 12

In this series of reactions the effect of solvent in the reaction was studied. It was observed the solvent causes a decrease in ethanol selectivity; surprisingly, addition of dimethylformamide resulted in no ethanol formation.

The reactions were carried out as described in Example 1. In each reaction the following reactants were used:

| | |
|---|---|
| $Rh(CO)_2$ acac | 2 mmol |
| $RuCl_3$ hydrate | 0.82 g |
| Ligand | 4 mmol |
| $CH_3I$ | 40 mmol |
| Methanol | 20 mL |
| Solvent | 20 mL |

The ligand was 1,3-bis(diphenylphosphino)propane, reaction time was two hours, temperature was 140° C. and pressure 975 psig±25 psig. The results are summarized in Table IX.

TABLE IX

| Run | Solvent | Synthesis Gas Uptake, psig | Ethanol Selectivity, M % |
|---|---|---|---|
| a | None | 3000 | 76.2 |
| b | DIETHYLCARBITOL | 1540 | 57.3 |
| c | Diglyme | 2030 | 70.9 |
| d | 1,4-Dioxane | 380 | 14.9 |
| e | Diphenyl ether | 1720 | 56.5 |
| f | N—Methyl pyrrolidinone | 1000 | 45.7 |
| g | Toluene | 1490 | 44.4 |
| h | Dimethyl formamide | 320 | 0 |

EXAMPLE 13

The effect of the presence of a secondary ligand on the process of this invention was studied in the series of reactions reported in this example. It was found that in some instances its addition to the catalyst mixture increased the activity, ethanol selectivity and catalyst longevity.

The reactions were carried out as described in Example 1. In Runs (a) to (f) the following reactants were used:

| | |
|---|---|
| $Rh(CO)_2$ acac | 2 mmol |
| $RuCl_3$ hydrate | 0.82 g |
| Ligand (L) | 4 mmol |
| Secondary ligand (SL) | as indicated |
| $CH_3I$ | 40 mmol |

-continued

| Methanol | mL | 40 |

Ligand: 1,3-bis(diphenylphosphino)propane (dppp)
Secondary ligand:
A = triphenylphosphine
B = tricyclohexylphosphine In Runs (g) to (h) a complex of the Rh(CO)$_2$acac and the 1,3-bis(diphenylphosphine)propane was used; it was prepared as described in Example 4. The results are summarized in Table X.

TABLE X

| Run | SL | L:SL Molar Ratio | Synthesis Gas Uptake, psig | Ethanol Selectivity M % |
|---|---|---|---|---|
| a | A | 2:1 | 2888 | 75.7 |
| b | A | 2:2 | 2770 | 74.9 |
| c | B | 2:0.5 | 3581 | 85.1 |
| d | B | 2:1 | 4150 | 70.8 |
| e | B | 2:3 | 2945 | 80.3 |
| f* | B | 2:1 | 2500 | 85.8 |
| g* | B | 2:3 | 2792 | 84.6 |
| h* | B | 2:4 | 2400 | 80.9 |

*Rh charged as 2.0 mmol Rh[1,3-bis(diphenylphosphino)-propane]$_2$Cl

EXAMPLE 14

The autoclave was charged with 0.52 g of Rh(CO)$_2$acac (2 mmol), 0.82 g of ruthenium trichloride hydrate, 0.94 g of 1,3-bis(di-p-tolylphosphino)propane (2 mmol) prepared in the laboratory, 2.5 mL methyl iodide (40 mmol) and 40 mL methanol. Following the procedure described in Example 1 the reactor contents were heated to 140° C. and the pressure was adjusted to 975±25 psig with a H$_2$:CO mixture having a 2:1 mole ratio. Gas uptake ceased after 1 hour in this period 1200 psig of synthesis gas was consumed. The autoclave was cooled to 19° C. and the pressure reduced to 0 psig. An aliquot of the liquid product was removed from the reactor and analysis indicated the formation and presence of the following compounds:

| | Area Percent |
|---|---|
| Ethanol: | 12.2% |
| Acetaldehyde | 5.2% |
| Ethyl acetate | 1.4% |
| Methyl acetate: | 10.6% |
| Acetic acid | 1.2% |
| Dimethyl acetal | 2.5% |
| Diethyl ether | 0.2% |
| Dimethyl ether | 10.2% |
| Methanol | 49.9% |
| Methyl iodide | 3.6% |

The selectivity to realizable ethanol was 53%.

The autoclave was then charged with an additional 20 mL of methanol and 20 mmol of methyl iodide to the original reactor contents. The reactor contents were heated to 140° C. and the pressure was adjusted to 975±25 psig with a H$_2$ CO mixture having a 2:1 mole ratio. Gas uptake ceased after 1.3 hours; in this period 1786 psig of synthesis gas was consumed. the autoclave was cooled to 19° C. and the pressure reduced to 0 psig. An aliquot of the liquid product was removed from the reactor and analysis indicated the formation and presence of the following compounds:

| | Area Percent |
|---|---|
| Ethanol | 24.0% |
| Acetaldehyde | 6.9% |
| Ethyl acetate | 4.8% |
| Methyl acetate | 12.1% |
| Acetic acid | 3.8% |
| Dimethyl acetal | 0.4% |
| Diethyl ether | 0.6% |
| Dimethyl ether | 9.2% |
| Methanol | 33.2% |
| Mehtyl iodide | 2.8% |

The selectivity to realizable ethanol was 61%.

The reactor contents were again heated to 140° C. and the pressure was adjusted to 975±25 psig with a H$_2$ CO mixture having a 2:1 mole ratio. The reaction was continued for 2.5 hours; in this period 1339 psig of synthesis gas was consumed and then arbitrarily stopped. The autoclave was cooled to 19° C. and the pressure reduced to 0 psig. An aliquot of the liquid product was removed from the reactor and analysis indicate the formation and presence of the following compounds:

| | Area Percent |
|---|---|
| Ethanol | 29.6% |
| Acetaldehyde | 8.7% |
| Ethyl acetate | 15.9% |
| Methyl acetate | 8.7% |
| Acetic acid | 13.1% |
| Dimethyl acetal | 0.02% |
| Diethyl ether | 2.2% |
| Dimethyl ether | 6.1% |
| Methanol | 10.8% |
| Methyl iodide | 1.4% |

The autoclave was then charged with an additional 20 mL of methanol and 20 mmol of methyl iodide to the original reactor contents. The reactor contents were heated to 140° C. and the pressure was adjusted to 975±25 psig with an H$_2$:CO mixture having a 2:1 mole ratio. The reaction was continued for 2.8 hours, during which period 1032 psig of synthesis gas was consumed, and then arbitrarily stopped. The autoclave was cooled to 19° C. and the pressure reduced to 0 psig. An aliquot of the liquid product was removed from the reactor and analysis indicated the formation and presence of the following compounds:

| | Area Percent |
|---|---|
| Ethanol | 22.6% |
| Acetaldehyde | 14.3% |
| Ethyl acetate | 16.7% |
| Methyl acetate | 8.4% |
| Acetic acid | 14.2% |
| Dimethyl acetal | 0.00 |
| Diethyl ether | 4.3% |
| Dimethyl ether | 7.9% |
| Methanol | 5.9% |
| Methyl iodide | 2.5% |

The selectivity to realizable ethanol was 61%.

The $^{31}$P nmr analysis of the catalyst residue showed that the ligand was coordinated to the rhodium. This example shows that the catalyst system containing rhodium atom, ruthenium atom, iodide atom and bis(diorganophosphino)alkane ligand (i.e., 1,3-bis(di-p-tolylphosphino)propane) selectively generates realizable ethanol under mild reaction conditions. It also shows that these catalysts have good stability and can be used repeatedly without loss of selectivity.

EXAMPLE 15

The autoclave was charged with 0.52 g of Rh(CO)$_2$acac (2 mmol), 0.82 g of ruthenium trichloride hydrate, 0.82 g of 1,3-bis(diphenylphosphino)propane (2 mmol), 2.5 mL of methyl iodide (40 mmol) and 40 mL of methanol. Following the procedure described in Example 1 the reactor contents were heated to 140° C. and the pressure was adjusted to 975±25 psig with a H$_2$:CO mixture having a 2:1 mole ratio. The reaction was continued for 2.5 hours, during which period 2833 psig of synthesis gas was consumed, and then arbitrarily stopped. The autoclave was cooled to 19° C. and the pressure reduced to 0 psig. An aliquot of the liquid product was removed from the reactor and analysis indicated the formation and presence of the following compounds:

|  | Area Percent |
|---|---|
| Ethanol | 37.0% |
| Acetaldehyde | 6.9% |
| Ethyl acetate | 4.0% |
| Methyl acetate | 5.8% |
| Acetic acid | 2.2% |
| Dimethyl acetal | 0.2% |
| Diethyl ether | 1.3% |
| Dimethyl ether | 6.8% |
| Methanol | 29.1% |
| Methyl iodide | 1.9% |

The selectivity to realizable ethanol was 80%.

The autoclave was then charged with an additional 20 mL of methanol and 20 mmol of methyl iodide to the original reactor contents. The reactor contents were heated to 140° C. and the pressure was adjusted to 975° C.±25 psig with a H$_2$:CO mixture having a 2:1 mole ratio. The reaction was continued for 1.75 hours, during which period 1482 psig of synthesis gas was consumed, and then arbitrarily stopped. The autoclave was cooled to 19° C. and the pressure reduced to 0 psig. An aliquot of the liquid product was removed from the reactor and analysis indicated the formation and presence of the following compounds:

|  | Area Percent |
|---|---|
| Ethanol | 32.8% |
| Acetaldehyde | 10.2% |
| Ethyl acetate | 4.6% |
| Methyl acetate | 6.7% |
| Acetic acid | 3.9% |
| Dimethyl acetal | 0.2% |
| Diethyl ether | 1.7% |
| Dimethyl ether | 9.3% |
| Methanol | 25.2% |
| Methyl iodide | 2.5% |

The selectivity to realizable ethanol was 75%.

The reactor contents were charged with an additional 20 mL of methanol, again heated to 140° C. and the pressure was adjusted to 975±25 psig with a H$_2$:CO mixture having a 2:1 mole ratio. The reaction was continued for 4 hours, during which period 3028 psig of synthesis gas was consumed, and then arbitrarily stopped. The autoclave was cooled to 19° C. and the pressure reduced to 0 psig. An aliquot of the liquid product was removed from the reactor and analysis indicated the formation and presence of the following compounds:

|  | Area Percent |
|---|---|
| Ethanol | 31.0% |
| Acetaldehyde | 15.9% |
| Ethyl acetate | 7.2% |
| Methyl acetate | 7.0% |
| Acetic acid | 4.0% |
| Dimethyl acetal | 0.1% |
| Diethyl ether | 3.0% |
| Dimethyl ether | 10.5% |
| Methanol | 16.9% |
| Methyl iodide | 1.8% |

The selectivity to realizable ethanol was 75%.

The autoclave contents were then emptied into a flask and the volatile materials distilled away under vacuum. The resulting solids were then placed back into the autoclave and the autoclave was also charged with 40 mL methanol and 2.5 mL 40 mmol) of methyl iodide. The reactor contents were heated to 140° C. and the pressure was adjusted to 975±25 psig with a H$_2$:CO mixture having a 2:1 mole ratio. The reaction was continued for 2.5 hours, during which period 2389 psig of synthesis gas was consumed, and then arbitrarily stopped. The autoclave was cooled to 19° C. and the pressure reduced to 0 psig. An aliquot of the liquid product was removed from the reactor and analysis indicated the formation and presence of the following compounds:

|  | Area Percent |
|---|---|
| Ethanol | 28.7% |
| Acetaldehyde | 9.7% |
| Ethyl acetate | 3.8% |
| Methyl acetate | 7.5% |
| Acetic acid | 2.0% |
| Dimethyl acetal | 0.3% |
| Diethyl ether | 1.0% |
| Dimethyl ether | 9.7% |
| Methanol | 28.7% |
| Methyl iodide | 3.6% |

The selectivity to realizable ethanol was 73%.

The $^{31}$P nmr analysis of the catalyst residue showed that the ligand was coordinated to the rhodium. This example shows that the catalyst system containing rhodium atom, ruthenium atom, iodide atom and 1,3-bis(diorganophosphino)alkane ligand [i.e., bis(diphenylphosphino)propane] selectively generates realizable ethanol under mild reaction conditions. It also shows that these catalysts have good stability and can be used repeatedly without loss of selectivity.

What I claim is:

1. A process for the reaction of an alcohol of the general formula R'OH, wherein R' is a monovalent hydrocarbyl (i) alkyl group having from 1 to 20 carbon atoms, (ii) alkenyl group having from 2 to 20 carbon atoms, or (iii) aralkyl group in which the aryl moiety is phenyl or naphthyl and the alkyl moiety has from 1 to 10 carbon atoms, with synthesis gas to selectively produce realizable alcohol; said process conducted at a temperature of from 50° C. to 250° C., a pressure of from 100 psig to 10,000 psig, wherein said synthesis gas has a H$_2$:CO mole ratio of 1:10 to 10:1, in contact with a rhodium-based catalyst system containing rhodium atom, ruthenium atom, iodine atom and a bis(diorganophosphino)alkane ligand of the general formula R₂PXPR₂, wherein X is a linear or branched alkyl, alkenyl or cyclic divalent bridge connecting the two P atoms, the terminal bonds of said bridge being from 1 to 10 carbon atoms apart and R is (i) a hydrogen atom with the proviso not more than one hydrogen atom is attached to a P atom, or (ii) an alkyl group having from 1 to 20 carbon atoms or (iii) an aryl, aralkyl or alkaryl group having 6 to 20 carbon atoms in the aryl moiety and from 1 to 10 carbon atoms in the alkyl-moiety; wherein the mole ratio of rhodium to alkanol is from 1:25 to 1:2500, the mole ratio of rhodium to ruthenium is from 1:10 to 10:1, the mole ratio of rhodium to iodine is from 1:500 to 500:1 and the mole ratio of rhodium to R₂PXPR₂ is from 1:100 to 100:1.

2. A process as claimed in claim 1, wherein the temperature is from 110° C. to 160° C., the pressure is from 500 psig to 2,500 psig and the H₂:CO mole ratio is from 1:5 to 5:1.

3. A process as claimed in claim 1, wherein R'OH is an alkanol having from 1 to 4 carbon atoms.

4. A process as claimed in claim 3, wherein the alkanol is methanol.

5. A process as claimed in claim 1, wherein said bis(diorganophosphino)alkane is a bis(dialkylphosphino)alkane wherein the alkyl group contains 1 to 10 carbon atoms and the bridging alkane group contains 2 to 6 carbon atoms.

6. A process as claimed in claim 1, wherein said bis(diorganophosphino)alkane is a bis(diarylphosphino)alkane wherein the aryl group is a phenyl group and the bridging alkane group contains 2 to 6 carbon atoms.

7. A process as claimed in claim 1, wherein said bis(diorganophosphino)alkane is a bis(alkyl arylphosphino)alkane wherein the alkyl group contains 2 to 5 carbon atoms, the aryl group is a phenyl group and the bridging alkane group contains 2 to 6 atoms.

8. The process as claimed in claim 1, wherein the mole ratio of rhodium to ruthenium is from 1:3 to 3:1 and the mole ratio of rhodium to R₂PXPR₂ is from 1:2 to 2:1.

9. The process as claimed in claim 1, wherein a secondary ligand is also present during the homologation.

10. The process as claimed in claim 1, wherein methanol is reacted with synthesis gas having a H₂:CO mole ratio of 1:5 to 5:1 at a temperature of from 110° C. to 160° C., a pressure of from 500 psig to 2,500 psig and the 1,3-bis(diorganophosphino)alkane is a 1,3-bis(diorganophosphino)propane.

11. The process as claimed in claim 10, wherein said 1,3-bis(diorganophosphino)propane is bis(diphenylphosphino)propane and the rhodium compound charged is rhodium dicarbonyl acetylacetonate.

12. The process as claimed in claim 10, wherein said 1,3-bis(diorganophosphino)propane is Rh[1,3-bis(diphenylphosphino)propane]₂Cl.

13. The process as claimed in claim 10, wherein said 1,3-bis(diorganophosphino)propane is 1,3-bis[-di(isobutylphenylphosphino)]propane.

14. The process as claimed in claim 1, wherein said bis(diorganophosphino)alkane is a 1,3-bis(diarylphosphino)propane.

15. The process as claimed in claim 14, wherein said 1,3-bis(diarylphosphino)propane is 1,3-bis(diphenylphosphino)propane.

16. The process as claimed in claim 14, wherein the alcohol reacted is methanol.

17. The process as claimed in claim 1, wherein said bis(diorganophosphino)alkane is a complex of a rhodium compound and a 1,3-bis(diarylphosphino)propane.

18. The process as claimed in claim 17, wherein said complex is Rh[1,3-bis(diphenylphosphino)propane]₂Cl.

19. The process as claimed in claim 1, wherein said bis(diorganophosphino)alkane is a 1,3-bis[di(aryl alkylphosphino)]propane.

20. The process as claimed in claim 17, wherein said 1,3-bis[di(aryl alkylphosphine)]propane is 1,3-bis-(isobutylphenylphosphino)propane.

21. The process as claimed in claim 1, wherein said bis(diorganophosphino)alkane is represented by the formula:

R₂P(CH₂)₃PR₂ wherein R is as defined in claim 1.

22. The process as claimed in claim 21, wherein R is a member of the group consisting of methyl, ethyl, cyclohexyl or phenyl.

23. The process as claimed in claim 1, wherein said bis(diorganophosphino)alkane is represented by the formula:

R(Ph)P(CH₂)₃P(Ph)R wherein Ph is phenyl and R is as defined in claim 1 with the proviso it is not the phenyl group.

24. The process as claimed in claim 23, wherein R is a member of the group consisting of hydrogen, methyl, ethyl, amyl or cyclohexyl.

25. The process as claimed in claim 1, wherein said bis(diorganophosphino)alkane is represented by the formula:

R₂P(CH₂)₃PPh₂ wherein Ph is phenyl and R is as defined in claim 1 with the proviso it is not the phenyl group.

26. The process as claimed in claim 25, wherein R is a member of the group consisting, ethyl or amyl.

27. The process as claimed in claim 1, wherein said bis(diorganophosphino)alkane is represented by the formula:

R(Ph)P(CH₂)₃PPh₂ wherein Ph is phenyl and R is as defined in claim 1 with the proviso it is not the phenyl group.

28. The process as claimed in claim 27, wherein R is a member of group consisting of methyl, n-propyl, n-octyl or cyclohexyl.

* * * * *